(12) United States Patent
Kline et al.

(10) Patent No.: US 11,311,238 B2
(45) Date of Patent: Apr. 26, 2022

(54) ATTACHABLE SENSING POD COMPRISING A PIEZOELECTRIC UNIT

(71) Applicant: CVR Global, Inc., Denver, NC (US)

(72) Inventors: Bret Kline, Columbus, OH (US); Peter Bakema, Denver, NC (US)

(73) Assignee: CVR Global, Inc., Denver, NC (US)

( * ) Notice: Subject to any disclaimer, the term of this patent is extended or adjusted under 35 U.S.C. 154(b) by 314 days.

(21) Appl. No.: 16/469,262

(22) PCT Filed: Dec. 14, 2017

(86) PCT No.: PCT/US2017/066329
§ 371 (c)(1),
(2) Date: Jun. 13, 2019

(87) PCT Pub. No.: WO2018/112157
PCT Pub. Date: Jun. 21, 2018

(65) Prior Publication Data
US 2020/0015748 A1 Jan. 16, 2020

Related U.S. Application Data

(60) Provisional application No. 62/434,042, filed on Dec. 14, 2016.

(51) Int. Cl.
*A61B 5/00* (2006.01)
*A61B 5/02* (2006.01)
(Continued)

(52) U.S. Cl.
CPC ........ *A61B 5/6832* (2013.01); *A61B 5/02007* (2013.01); *A61B 7/04* (2013.01);
(Continued)

(58) Field of Classification Search
CPC . A61B 5/04288; A61B 5/04085; A61B 5/681; A61B 5/6804; A61B 5/02416;
(Continued)

(56) References Cited

U.S. PATENT DOCUMENTS 8,320,576 B1 * 11/2012 Abbruscato .............. A61B 7/04
381/67
11,100,737 B1 * 8/2021 Goldstein .......... A61N 1/36034
(Continued)

FOREIGN PATENT DOCUMENTS

CN 104618826 A * 5/2015
JP 2012090909 A * 5/2012

*Primary Examiner* — Matthew A Eason
*Assistant Examiner* — Kuassi A Ganmavo
(74) *Attorney, Agent, or Firm* — Vos-IP, LLC

(57) ABSTRACT

A sensor pod assembly comprising a gel pad, a gel pad cap, a piezoelectric sensor, a base plate, a base plate support, a wiring harness, a battery, a noise attenuating backing, and a charging component; said gel pad comprising a top and bottom, said bottom having a flat bottom and a concave recess; said flat bottom acoustically contacting said piezoelectric sensor; said piezoelectric sensor secured to a first side of said base plate support, and a second side of said base plate support secured to said base plate, a wiring harness and a battery connected to said base plate, and a charging component having exposed annular rings on the exterior side of said sensor pod assembly; a noise attenuating backing compressing the charging component against the base plate; and a gel pad cap having an outer face and an inner face, said inner face in contact with said base plate support.

9 Claims, 15 Drawing Sheets

(51) Int. Cl.
*A61B 7/04* (2006.01)
*G01H 11/08* (2006.01)
*H04R 1/04* (2006.01)
*H04R 1/42* (2006.01)
*H04R 1/46* (2006.01)
*H04R 17/02* (2006.01)
*B06B 1/06* (2006.01)
*A61B 5/024* (2006.01)

(52) U.S. Cl.
CPC ............... *G01H 11/08* (2013.01); *H04R 1/04* (2013.01); *H04R 1/42* (2013.01); *H04R 1/46* (2013.01); *H04R 17/02* (2013.01); *A61B 5/02416* (2013.01); *A61B 5/681* (2013.01); *A61B 5/6804* (2013.01); *B06B 1/0603* (2013.01)

(58) Field of Classification Search
CPC ..... A61B 5/6835; A61B 5/02007; A61B 7/04; G01H 11/08; H04R 1/04; H04R 1/42; H04R 1/46; H04R 17/02; G01L 1/2206; B06B 1/0603
See application file for complete search history.

(56) References Cited

U.S. PATENT DOCUMENTS

| | | | |
|---|---|---|---|
| 2009/0015101 A1 | 1/2009 | Petersen et al. | |
| 2010/0234716 A1* | 9/2010 | Engel | A61B 5/02055 600/391 |
| 2010/0326211 A1* | 12/2010 | Stein | A61B 5/6846 73/862.636 |
| 2011/0166459 A1* | 7/2011 | Kopetsch | A61B 5/02125 600/485 |
| 2012/0078071 A1 | 3/2012 | Bohm et al. | |
| 2012/0232427 A1* | 9/2012 | Bakema | A61B 7/04 600/586 |
| 2013/0030259 A1* | 1/2013 | Thomsen | A61B 5/02028 600/301 |
| 2015/0057512 A1* | 2/2015 | Kapoor | A61B 5/0205 600/324 |
| 2016/0100817 A1* | 4/2016 | Hussain | A61B 7/04 600/301 |
| 2016/0192856 A1 | 7/2016 | Lee | |
| 2018/0055359 A1* | 3/2018 | Shamim | A61B 5/14539 |

* cited by examiner

ATTACHABLE SENSING POD COMPRISING A PIEZOELECTRIC UNIT

CROSS-REFERENCE TO RELATED APPLICATIONS

This application is a 371 of PCT Application No. PCT/US2017/066329, filed Dec. 14, 2017, which claims the benefit of U.S. Provisional Patent Application No. 62/434,042 filed on Dec. 14, 2016, the contents of which are incorporated herein by reference in their entirety.

FIELD OF INVENTION

The present application is generally related to an attachable sensor pod that can be selectively attached to a patient for detecting certain vortices in the body, wherein said attachable sensor pod comprises a piezoelectric component that is utilized to detect, measure, and record certain vortices in the body so as to determine stenosis in the arterial system.

BACKGROUND OF THE INVENTION

US 2012/0232427 describes a sensor, sensor pad and sensor array for detecting infrasonic acoustic signals. The '427 generally describes several sensor pods and particularly the use of a piezo electric unit to detect infrasonic acoustic signals from a body.

Piezoelectric units function based on the occurrence of electric depose moments in solids. The solid may be either induced for ions on crystal lattice sites with asymmetric charge surroundings or may directly be carried by molecular groups. The dipole density or polarization may be calculated by summing up the dipole moment per volume of the crystallographic unit cell.

Piezoelectric sensors (also referred to as a "Piezo") have a variety of potential uses, but as described herein, they are being utilized as a microphone. The principal of operation of a piezoelectric sensor is that a physical dimension, transformed into a force, acts on two opposing faces of the sensing element. Detection of pressure variations in the form of sound is the most common sensor application, e.g. acting as a microphone, wherein the sound waves bend the piezoelectric material creating changing voltage. Accordingly, the piezo sensor can be placed on or near a sound to receive the sounds.

Piezo sensors are especially used with high frequency sound in ultrasonic transducers for medical imaging and industrial nondestructive testing. However, piezo sensors are also frequently used for the detection and activation of a device, based on the ability to receive a signal and to then send an electronic signal, thereby acting as the actuator.

SUMMARY OF THE INVENTION

A sensor pod assembly comprising: a base plate; an electronic circuitry; a piezoelectric device; a pair of O-rings; a gel pad and a gel pad cap; wherein attached to the base plate is the electronic circuitry, including a battery, a wireless connection device, and memory suitable to electronically run the sensor pod; the first O-ring of the pair of O-rings is positioned on the base plate and a piezoelectric unit is positioned on the O-ring; the second O-ring of the pair of O-rings is positioned above the piezoelectric unit so as to sandwich the piezoelectric unit between the pair of O-rings; a gel pad having a piezo contacting surface and a skin facing surface; wherein the piezo contacting surface is in contact with a first side of the piezo electric unit; and a gel pad cap attached to the base plate with corresponding threaded components on the base plate and the gel pad cap, so as to secure the gel pad into place.

The sensor pod wherein the gel pad cap is constructed having a sound attenuating material disposed within a shell.

The sensor pod wherein a sound attenuating material is further disposed of within the circumference of the O-rings and between the base plate and the piezo electric unit.

The sensor pod wherein a sound attenuating material is further disposed of between the O-rings and the gel pad cap.

The sensor pod wherein the gel pad and the gel pad cap are a single disposable unit, wherein the gel pad is attached to the gel pad cap.

The sensor pod wherein the gel pad comprises an adhesive on the skin facing surface.

A sensor pod assembly comprising: a base plate; an electronic circuitry; a piezoelectric device; a pair of O-rings; a gel pad and a gel pad cap; wherein attached to the base plate is the electronic circuitry, including a battery, a wireless connection device, and memory suitable to electronically run the sensor pod; the first O-ring of the pair of O-rings is positioned on the base plate and a piezoelectric unit is positioned on the O-ring; the second O-ring of the pair of O-rings is positioned above the piezoelectric unit so as to sandwich the piezoelectric unit between the pair of O-rings; a gel pad having a piezo contacting surface and a skin facing surface; wherein the piezo contacting surface is in contact with a first side of the piezo electric unit; and a gel pad cap attached to the base plate with corresponding threaded components on the base plate and the gel pad cap, so as to secure the gel pad into place.

In a preferred embodiment, the gel pad cap is constructed having a sound attenuating material disposed within a shell.

In a preferred embodiment, wherein a sound attenuating material is further disposed of with the circumference of the O-rings and between the base plate and the piezo electric unit.

In a further embodiment, wherein a sound attenuating material is further disposed of between the O-rings and the gel pad cap.

In a further embodiment, wherein the gel pad and the gel pad cap are a single disposable unit, wherein the gel pad is attached to the gel pad cap.

In a further embodiment, wherein the gel pad comprises an adhesive on the skin facing surface.

In a further embodiment, a sensor pod assembly comprising: a base plate having a top side and a bottom side, a piezoelectric unit, a battery, a noise attenuating backing, a wireless charging coil, a sound attenuating cap, and a sensor pad, said base plate comprising electronic circuitry connected to said battery, said piezoelectric unit and to said wireless charging coil, said piezoelectric unit attached to said top side of said base plate and said wireless charging coil and said battery attached to said bottom side; said sound attenuating cap having a ring shape, having an inner and outer side wall and a circular opening providing access to the piezoelectric unit from the top side; and said noise attenuating backing engaged to the bottom side of the base plate; and said sensor pad positioned within the circular opening of said sound attenuating cap and in contact with at least a portion of the piezoelectric unit.

In a further embodiment, the sensor pod assembly further comprising a base plate support having a top and a bottom said base plate support bottom engaged to the top side of the base plate and said piezo attaching directly to the base plate support top.

In a further embodiment, the sensor pod assembly wherein said base plate support further comprises a securing ridge corresponding to a tab on said noise attenuating backing.

In a further embodiment, the sensor pod assembly wherein said sound attenuating cap comprises a securing component on an inner side having a paired securing component on said base plate support for selective attachment thereto.

In a further embodiment, the sensor pod assembly further comprising a sound attenuating material defined between the base plate bottom and said noise attenuating backing.

In a further embodiment, the sensor pod assembly comprising an adhesive contact between said piezoelectric assembly and said base plate support.

In a further embodiment, the sensor pod assembly wherein said wireless charging coil comprising a positive charging contact and a negative charging contact sandwiched around an insulating spacer.

A sensor pod assembly comprising: a base plate having a top and a bottom face; a base plate support having a top and bottom, an electronic circuitry; a piezoelectric device having a first side and a second side; a gel pad and a gel pad cap; wherein attached to the base plate is the electronic circuitry, including a battery, a wireless connection device, and memory suitable to electronically run the sensor pod; said bottom of the base plate support attached to the top face of the base plate, and said second side of said piezoelectric device attached to the top of the base plate support, a gel pad having a piezo contacting surface and a skin facing surface; wherein the piezo contacting surface is in contact with a first side of the piezo electric unit; and a gel pad cap comprising an outer layer and an inner layer, with said inner layer attached to the base plate with corresponding threaded components on the base plate and the inner layer of said gel pad cap.

In a further embodiment, the sensor pod assembly wherein said gel pad comprises a circumferential flange on the piezo contacting surface, said circumferential flange in intimate contact with said gel pad cap, thereby securing said gel pad into position.

In a further embodiment, a sensor pod assembly comprising a sensor pad, a sensor pad cap, a piezoelectric unit, a base plate, a base plate support, a battery, electronic circuitry, a sound attenuating material, a wireless charging coil, and noise attenuating backing; said base plate having a top side and a bottom side, said top side in intimate contact with a bottom side of said base plate support; a piezoelectric device attached to a top side of said base plate support; said sensor pad cap contacting a top side of said base plate support, outside of said piezoelectric device, and defining therebetween said base plate support and said sensor pad cap, a void filled with said sound attenuating material; said battery attached to said bottom side of said base plate and electronic circuitry connecting said battery and said piezo to said base plate, and said wireless charging coil secured to the bottom side of said base plate, with said noise attenuating backing defining a rear of said assembly.

In a further embodiment, a sensor pod assembly comprising a gel pad, a gel pad cap, a piezoelectric sensor, a base plate, a base plate support, a wiring harness, a battery, a noise attenuating backing, and a charging component; said gel pad comprising a top and bottom, said bottom having a flat bottom and a circumferential flange and said top having a concave recess; said flat bottom acoustically contacting said piezoelectric sensor; said piezoelectric sensor secured to a first side of said base plate support, and a second side of said base plate support secured to said base plate, a wiring harness and a battery connected to said base plate, and a charging component having exposed annular rings on the exterior side of said sensor pod assembly; a noise attenuating backing compressing the charging component against the base plate; and a gel pad cap having an outer face and an inner face, said inner face in contact with said base plate support.

In a further embodiment, the sensor pod assembly wherein said charging component comprises a first negative annular ring having a negative contact point, a spacer, and a positive annular ring having a positive contact point, wherein the negative annular ring and positive annular ring sandwich the spacer.

In a further embodiment, the sensor pod assembly wherein said negative annular ring and said positive annular ring are connected to said wiring harness.

In a further embodiment, the sensor pod assembly further comprising a sound attenuating material disposed of between said base plate and said noise attenuating backing.

In a further embodiment, the sensor pod assembly wherein said gel pad cap comprises threads on the interior face corresponding to threads on a portion of the base plate support, said threads providing for selective attachment of the gel pad cap to said base plate support.

A further embodiment is directed toward a method of determining stenosis comprising adhering a sensor pod to a patient and detecting sounds from a target artery, and determining stenosis based upon the detected sounds.

BRIEF DESCRIPTION OF THE FIGURES

FIGS. 6A, 6B, and C6 depict components of a sensor pod, wherein FIG. 6A depicts a front (patient) view of an alternate, contact charging sensor pod design and attached gel pad, FIG. 6B depicts a side view of an alternate, contact charging sensor pod design and attached gel pad.

DETAILED DESCRIPTION OF THE INVENTION

Piezoelectric sensors are highly sensitive detection devices that can be utilized to detect and record sounds at a huge range of frequencies and amplitudes. In certain devices, piezoelectric sensors can be utilized for detecting even the faintest sounds, which can then be recorded and analyzed for understanding of internal flow patterns in the arterial system. However, because of the low amplitude sounds that are being detected, any ambient noises or background noise can be fatal to accurately detecting and measuring the faint noises. Indeed, the ambient noises are sufficiently loud in most cases that they can irretrievably entangle the subtle noises for detection. In a sense, the noises to be detected become so small as to be lost.

The device described herein is a sensor pod having a piezoelectric unit that is part of a larger system or device for detecting and measuring vortices in the body, specifically in the arterial blood flow systems, wherein the sounds are detected, stored and can be analyzed to determine blockage in the arterial system.

Because of the highly sensitive nature of the piezoelectric units, having the pod attached to any number of components may introduce background noise error. Accordingly, in certain embodiments as described herein provides for a sensor pod that is adhered to the skin of a patient for detecting the sounds through the arterial system and transmits the sound data wireless via Bluetooth, WiFi, or similar wireless network(s) to a receiving device capable of recording and interpreting the sent data. Additionally, the sensor pod is powered via a built-in rechargeable battery that may be recharged wirelessly or via metal to metal contacts. This provides an opportunity to eliminate the use of a holding device that may introduce noise to the piezo. Accordingly, these devices can be directly placed on the body without a holding device. However, a holding device may be utilized in certain situations to assist with maintaining the device in a defined position.

Figure 1:
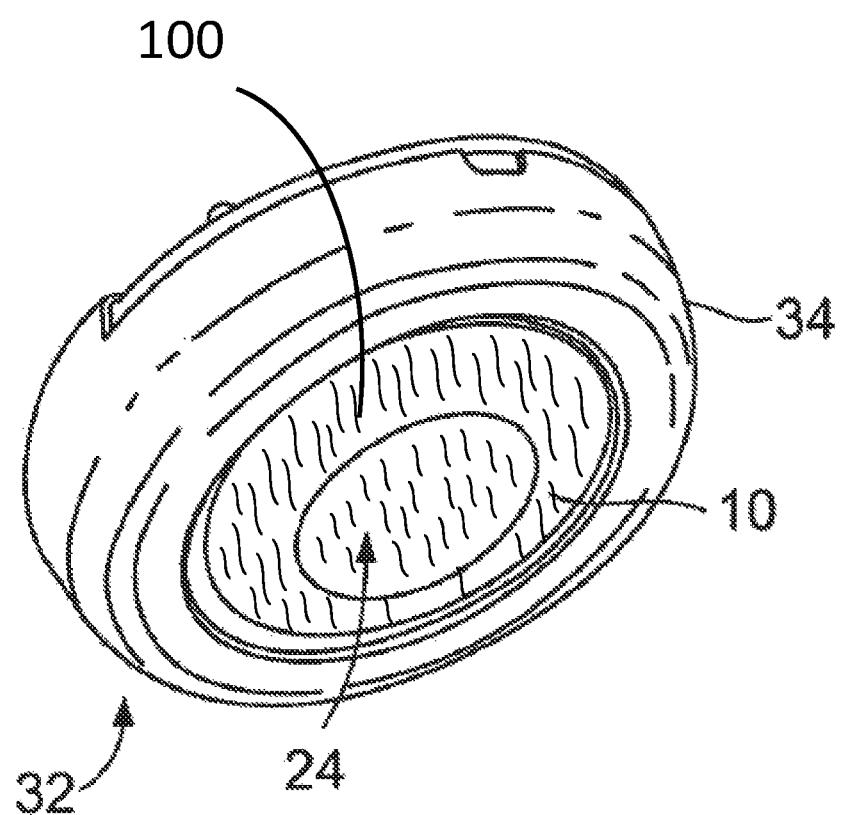
FIG. 1 depicts a sensor pod and attached gel pad.

The sensor pods are depicted in greater detail in the figures. FIG. 1 depicts a sensor pod 32 having an attached gel pad 10. The sensor pod 32 is circular in shape and has a pad cap 34. The pad cap 34 has several functions. First, it is intended to assist in holding the gel pad 10 to the piezoelectric unit (not depicted in FIG. 1). It aligns the gel pad 10 to the center of the piezoelectric unit (not depicted in FIG. 1). The pod cap 34 preferably screws onto the sensor pod 32, though other attachment mechanisms are suitable. In certain embodiments, for example, the pod cap 34 can compress and retain an edge of the gel pad 10 to hold it in place. In other embodiments, the pod cap 34 can simply reduce movement of the gel pad 10, where it is maintained on the piezoelectric unit with friction or an adhesive force between the piezoelectric unit and the gel pad 10 itself.

The gel pads 10 optionally comprise an adhesive 100 (such as a pressure sensitive adhesive) that is placed on one more of the skin facing side of the gel pad 10. The adhesive is utilized to adhere the gel pad to the skin surface of a patient. The adhesive can then be selectively removed from the skin surface and thus remove the gel pad 10 and the sensor pod. The types of adhesives for such use are available in the medical industry for numerous components that are necessary to be selectively adhered to the skin of a patient. Adhesives, for the purposes of this application, may also include conductivity gels typically comprising one or more of propylene glycol, glycerin, phenoxyethanol, and Carbopol polymers.

Figure 2A:
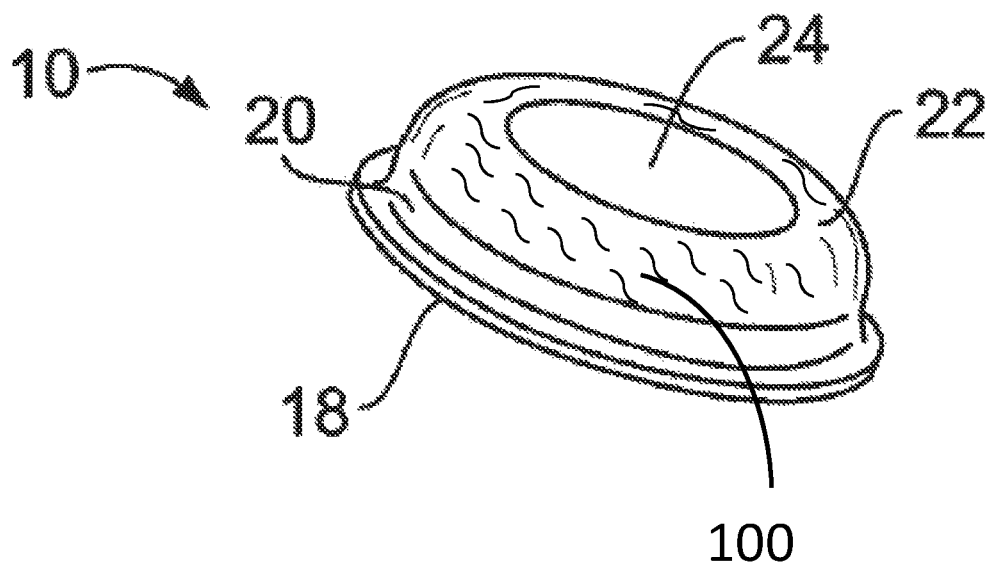
FIGS. 2A and 2B depict two variants of gel pads for selective attachment to a sensor pod having an adhesive thereon.
Figure 2B:
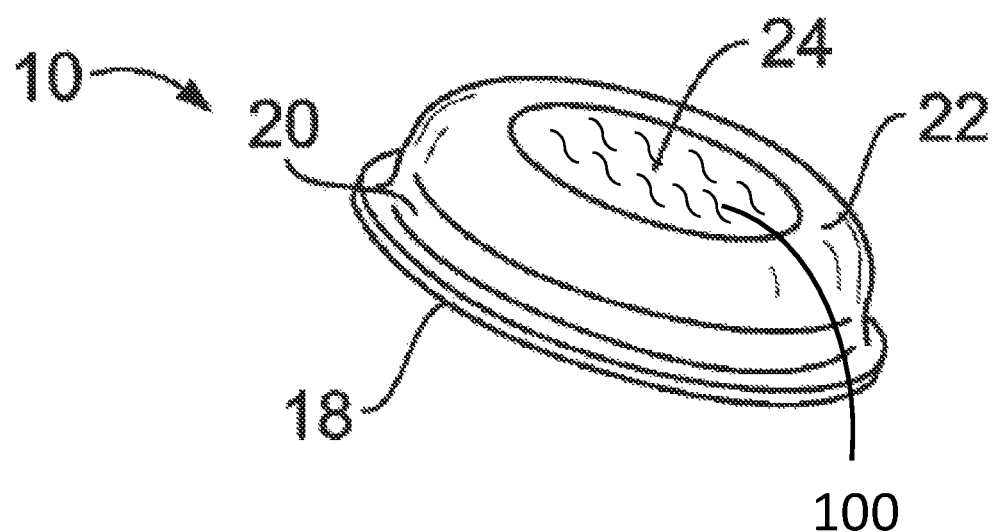
Figure 4:
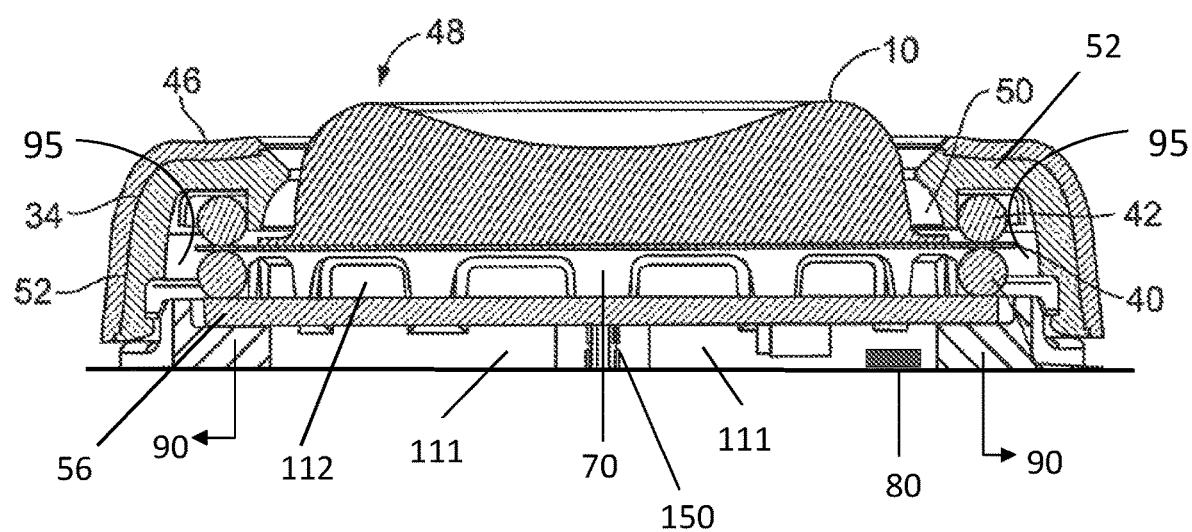
FIG. 4 depicts a cross sectional view of a sensor pod.

FIG. 2 provides additional examples of the adhesive 100 being placed onto the surface of the gel pad 10. In FIG. 1, the adhesive 100 is placed on substantially the entire top surface of the gel pad 10. In FIG. 2A, the gel pad 10 is placed only on the circular ridge 22 and surfaces, but not inside of the concave recess 24. By comparison, FIG. 2B depicts the adhesive 100 placed only inside the concave recess 24 of the gel pad. Certain gel pads 10 further comprises a circumferential flange 18 that assists with securing the gel pad 10 underneath the pod cap 34, as depicted in FIGS. 1 and 4, and against the piezoelectric unit. Furthermore, the side wall 20 of the gel pad 10 typically does not need any adhesive, as it will not be in contact with the skin surface.

Figure 3:
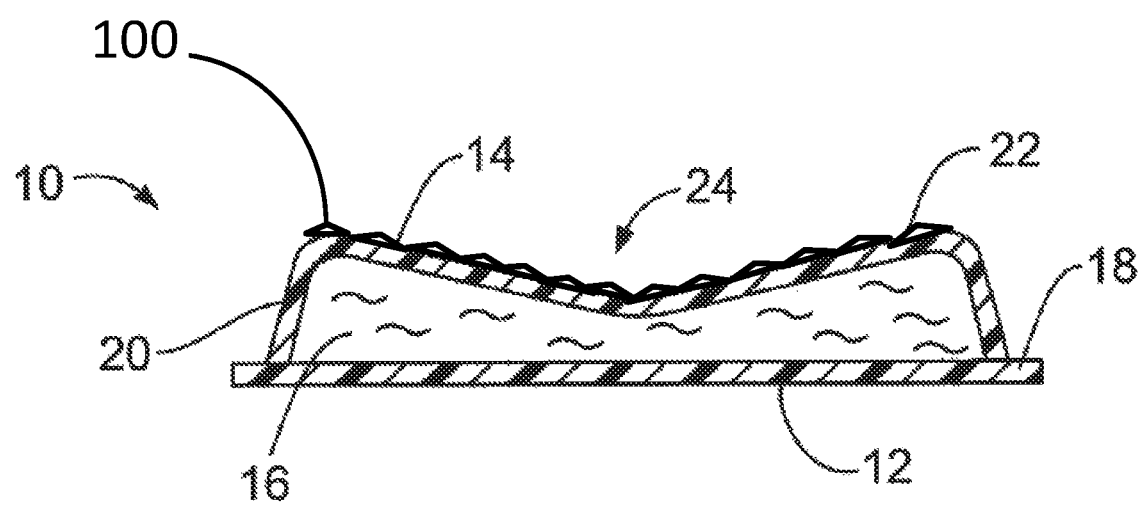
FIG. 3 depicts a cross-sectional view of a gel pad having an adhesive placed on the entire face.

FIG. 3 depicts a variant shape of the gel pad 10 in a cross-sectional view showing clearly the side wall 20 and the flange 18. The adhesive 100 is depicted as being provided on both the top circular ridge 22, and also in the concave recess 24. The shape of the gel pad 10 in FIG. 3 has a much sharper transition from the circular ridge 22 to the concave recess 24, as compared to those depicted in FIGS. 2A and 2B. Other suitable shaped gel pads are previously disclosed by the applicant and may be suitable for use herein, in for example U.S. Provisional Patent Application No. 62/350,617, filed Jun. 15, 2016 or US 2015/0320323. FIG. 3 further depicts the gel material 16 that is within the concave recess. In certain embodiments the gel pad 10 is made of a single material typically by molding. However, in other embodiments, the exterior of the gel pad 10, as identified by the striped lines, including the gel base 12, the flange 18, the side walls 20, the circular ridge 22 and the concave recess 24 are made of one material, typically a thermoformed or injection molded film, and a second transference material is injected into the center of the gel pad. This material assists with acoustical coupling between the skin and the piezoelectric unit.

Indeed, the sound properties are paramount in this invention. A second feature of the pod cap 34, as depicted in FIGS. 1, 2, and 4 is the ability to limit or reduce background noise or other sound pollution. Therefore, the pod cap 34 can be manufactured in a single piece or multi piece solid, cellular, or filled plastic, metal, or polymer material that can attenuate sound. However, in other embodiments, the pad cap 34 is manufactured having a sound attenuating structure in the cap. For example, FIG. 4 depicts that the pod cap 34 comprises an exterior shell 46 and an interior sound attenuating material 52. The exterior shell may be a rigid or compressible material, but should be easily cleaned for sanitary procedures, as it may, in some cases contact the skin of the patient.

The sound attenuating material 52 is depicted having a different structure than the exterior shell 46. For example, the structure may be an open or honeycomb like structure to reduce sound. Furthermore, a foam, gel, or additional material may be inserted or injected into a hollow portion of either or both of the exterior shell 46 or of the sound attenuating material 52, so as to create additional sound attenuating properties.

However, FIG. 4 further provides several additional features that are relevant to the sound attenuating properties of the invention as disclosed herein. For example, there is a void 50 between the gel pad 10 and the pod cap 34. This void 50 can be left without material or can be optionally provided with a sound attenuating material. For example, the gel pad 10 can be inserted and then a further gel material can be expressed around the side of the gel pad 10 to create a seal between the pod cap 34 and the gel pad 10. Otherwise, the void 50 can be simply filled with a sound attenuating material and connected to the inside lip of the pod cap 34.

In one embodiment, mounting of the piezo 40 is provided by elastomeric, electrically conductive, O-rings 42, to sandwich the piezoelectric unit 40. These torus structures are provided to specifically attenuate and separate noise and vibrations from the device and the piezoelectric unit 40 itself. Therefore, spaces like void 50 can be appropriately utilized with the necessary material to attenuate or reduce sound and background noise. Alternatively, nonconductive O-rings can be utilized where appropriate for electrically separating the components. Additional mounting mechanisms for the Piezo 40 are also suitable, such as with an adhesive, threaded fastener, or as otherwise described herein or as known to those of skill in the art.

A side cap void 95 is provided adjacent to the piezoelectric unit. Preferably this is left as a void so as to not contact any portion of the piezoelectric unit 40. Indeed, the torus structures as depicted assist in separating the piezoelectric unit 40 from the rest of the device.

Below the piezoelectric unit 40 is a sound attenuating barrier 70. This barrier provides for space between the piezoelectric unit itself and the base, thereby allowing the piezoelectric unit to vibrate and function as necessary. However, the attenuating barrier 70 is positioned on base barrier 56 made of the same or similar sound attenuating materials as described for the pad cap 34. Similarly, base void 112 can be left open or filled with an appropriate material for attenuating sound.

On each side of FIG. 4 is a rear barrier 90 that is in contact with the base barrier 56. This rear barrier 90, is a ring like structure that surrounds the base and is made of one or more sound attenuating material. By having a ring like structure, the rear barrier 90 provides for rear openings 111 that allow for several options. For example, the circuitry and components necessary to run the devices. For example, the electronic module 80 is positioned in this rear opening 111 and provides for the necessary circuitry to run the device, provide wireless connectivity features, and provide power, among other features. The electronic module 80 will include all the necessary features to run the device. Wires may run from the electronic module 80 through the wired stem 150, to connect to the piezoelectric unit 40. Additional wires may connect internal components and wireless features will then allow for transmission of data from the sensor pods to a base on control unit.

The sensor pods are preferably wirelessly charged through components in the electronic module 80 and a base charging station. However, suitable wired or contact points may also charge the internal batteries. Similarly, electronic contact points may also allow for transmission of data in place of wireless connectivity, or in addition to wireless connectivity.

Figure 5:
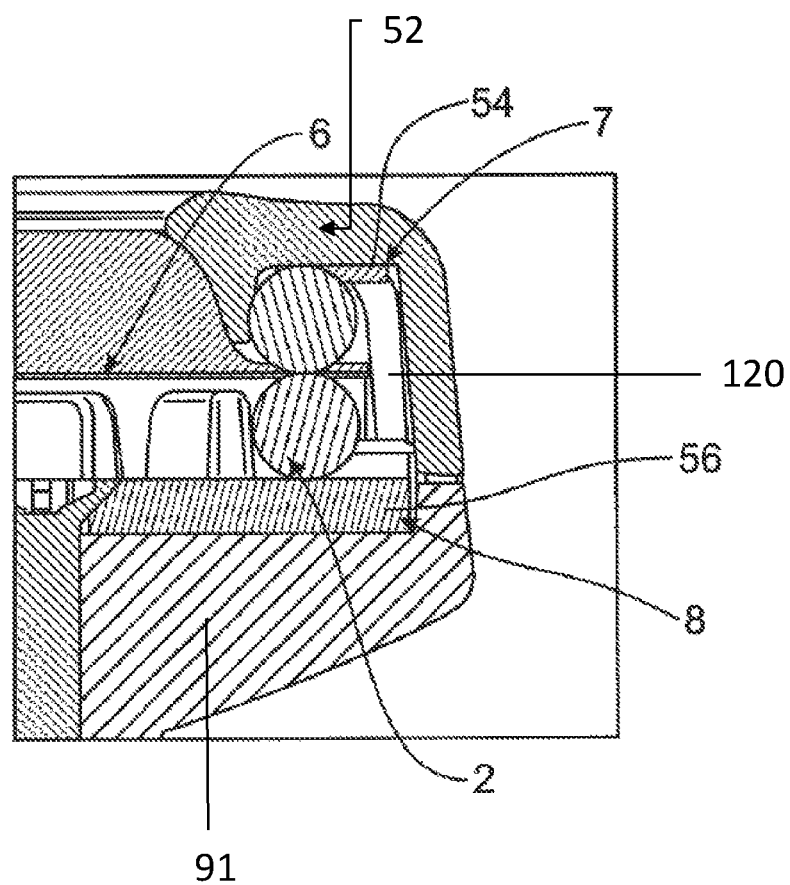
FIG. 5 depicts a cut out of a portion of the sensor pod and gel pad.

FIG. 5 provides a detailed depiction of a portion of one section of an embodiment of a sensor pod. For example, as compared to FIG. 4, a sound base 91 is provided that covers the rear portion of the base of the sensor pod. This sound base 91 is made of any number of suitable sound attenuation materials. The primary goal of the material is to isolate the piezoelectric device inside the sensor pod.

In a further embodiment, the pad cap 34 comprises an exterior shell or film and a hollow internal compartment, as depicted in FIG. 5. Accordingly, this hollow compartment can be suitably filled or injected with a sound attenuating material 52. Thus, the material can be injected after the shell is manufactured to allow for a great variety of materials that may not be suitable during the curing process.

As described above, the sound attenuating material 52 of the pad cap is depicted in direct contact with the gel pad 10. In this orientation, the surrounding materials of the sensor pod act much like a pair of over-the-ear headphones, in that they surround the area of skin and isolate sounds away from this area. Accordingly, background noise should be attenuated as much as reasonably possible to provide for greater clarity of the signal to improve the signal-to-noise ratio.

The piezoelectric sensor (piezo) itself is described in the above reference applications, each of which are incorporated herein by reference. Generally, piezo sensors have a diameter of 1.5". A range of 0.1" to about 12" is preferred, wherein the size of the piezo is related to the diameter of the fluid flow vessel to be measured. In preferred embodiments, the fluid flow vessels are veins and arteries in the body, and which a 1.5" or smaller diameter piezo is preferable.

There is no inherent frequency limit for a piezoelectric sensor. However, the limits of applications are usually determined by resonances associated with the shape and/or the size of the transducer design. The piezo sensors utilized herein, have a thickness of about 0.5 mm and are capable of detecting sounds between 10 Hz and 32 KHz and an amplitude of 0.0002 N/m2 to greater than 10 N/m2. In preferred embodiments, the piezo attached to a sensor pod detect sounds between about 20 to 3000 Hz, which are relevant towards measurements of fluid flow in the body. Typically, these sounds have an amplitude of between 0.002 N/m2 and 20 N/m2. While additional sounds are recorded, many of these sounds, i.e. the heartbeat and extraneous noise, are removed from the data set through several filters.

Indeed, it is known that the piezo elements wear over time and that damage can unfortunately occur from use. Because of the sensitive nature of the sensor pods, it is necessary to ensure that they are properly functioning before each use. Proper testing protocols utilize a program implemented through a computer, which generates a known set of sounds related to the sounds to be detected on the fluid flow vessel and matches the known played sound to the sounds detected and recorded in realtime by the sensor pods. Where the known sounds and detected sounds match, the sensor pod is confirmed to be working. Wherein the sensor pod is not functioning properly, the system will sound an alarm, which will indicate to the operator the need to replace the disposable component of the sensor pod.

Before the sensor pods are utilized, the piezoelectric sensors must be tested to confirm that they are functioning as intended. Because of the sensitive and fragile nature of the piezoelectric elements, there are several ways in which the piezoelectric elements can be damaged including ordinary and standard use of the device. Damage may occur as the piezoelectric element wears from ordinary and standard use, and after about 50 to about 400 uses, the piezoelectric element breaks down so that the function and the electrical currents generated are different when comparing the first use to the $100^{th}$, $200^{th}$, $300^{th}$, or $400^{th}$ use. Accordingly, to ensure that accurate results are received by each of the units, it is imperative to replace the unit that has worn to maintain consistent results.

Additional wear or breakage can occur to the piezoelectric sensors 40 by rough use of devices. For example, human error may lead to the devices being dropped, or placed onto a base or charging station improperly, that results in breaks, bends, or otherwise damages the piezoelectric unit.

Further damage may occur as clean sensor pads 10 are attached and placed against the piezoelectric sensor 40 for use on a patient. To ensure sanitary use of the device, the sensor pads 10 are replaced between each use of the device.

However, because the sensor pads 10 are placed directly onto the piezoelectric unit 40, there is risk that human error may damage the piezoelectric sensor, either by too much force, or simply through improper pressure applied to the sensor when installing or removing a sensor pad 10. However, as described above, some portions of the pod cap 34 may contact the skin of the patient and thus these components need to be either able to be sterilized or replaceable.

Indeed, in certain embodiments, the gel pad 10 and the pod cap 34 are a complete disposable unit that is manufactured with an adhesive on the skin facing side. A removable adhesive barrier is placed on this surface for transport and sanitary procedures and is removed before use. The pod cap 34 is thus attached to the gel pad, e.g. in FIG. 5, they are depicted as in contact, and can be adhered together at the contact points.

In certain embodiments, by screwing on the pod cap 34, the gel pad 10 is properly seated in the device. In certain embodiments, the flange 18 (as in FIGS. 2A and 2B) is in contact with the underside or interior side wall of the pod cap (sound attenuating cap). However, in other embodiments, the gel pad 10 flange 18 does not contact the pod cap 34, and instead is merely in contact with the top face of the piezo. In other embodiments, the gel pad 10 does not contain a flange 18.

A gel or electronic material 6 may be further provided on the piezoelectric unit to improve impedance measuring in certain embodiments, or alternatively, to aid in selectively adhering the gel pad 10 to the piezoelectric unit or to the skin of the patient. Accordingly, the gel can function as both an acoustic material as well as an adhesive.

Figure 6A:
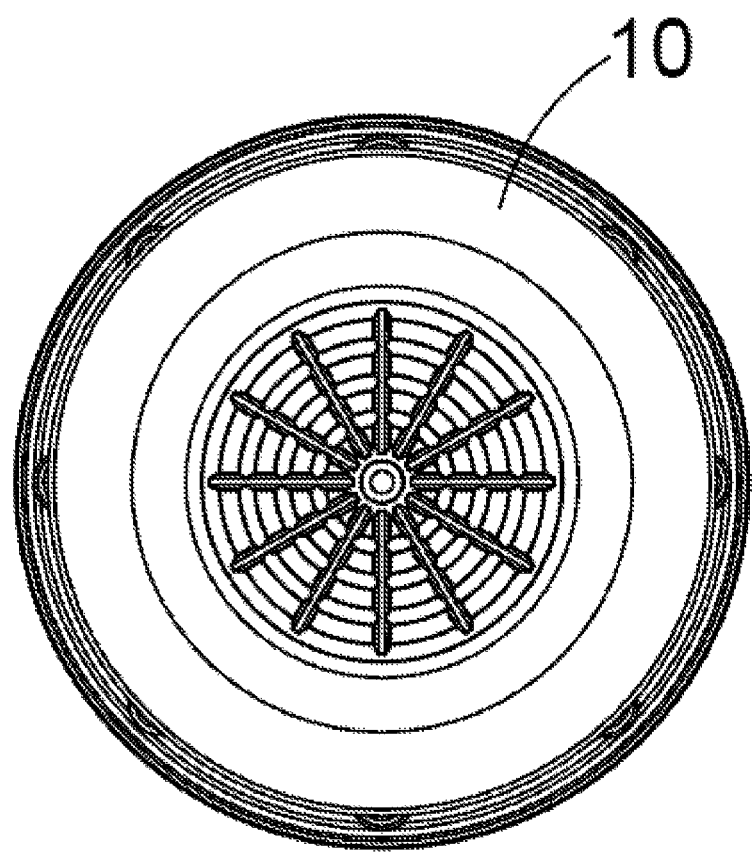
Figure 6B:
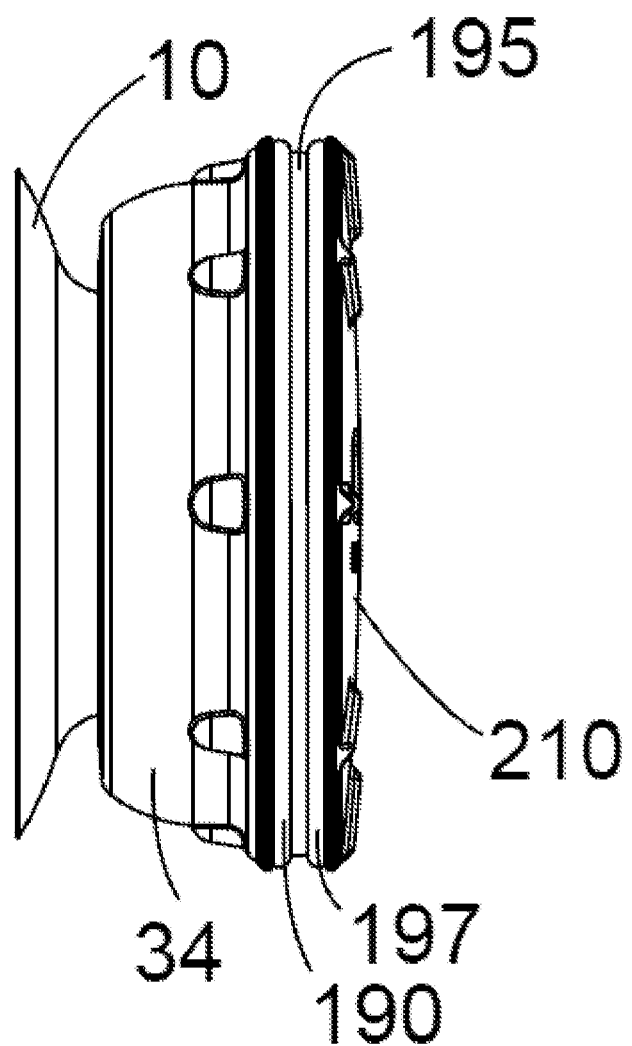
Figure 6C:
FIG. 6C depicts a rear view of an alternate, contact charging sensor pod design and attached gel pad.

FIG. 6A depicts a view of the device from the skin facing side of an alternative embodiment of the device. The gel pad 10 is depicted with a pattern thereon. FIG. 6B depicts a side view of the contact charging sensor pod. The side profile depicts a negative metal contact ring 190. This feature allows the device to be charged anywhere within 360 degrees around the device. This allows for simplicity in charging the device as the charging element can then be placed anywhere around the unit to be charged. This can be through induction charging or through contact charging, as appropriate. An insulating spacer 195 separates the contact rings 190 and 197. Indeed, the 190 ring is the negative, while the 197 ring is the positive. At the rear of the device is a rigid rear cap 210. This cap 210 is shown in detail in FIG. 6C with an ornamental design provided thereupon. The rear cap 210 provides noise attenuating features and is referred to in certain cases as a noise attenuating backing.

Figure 7A:
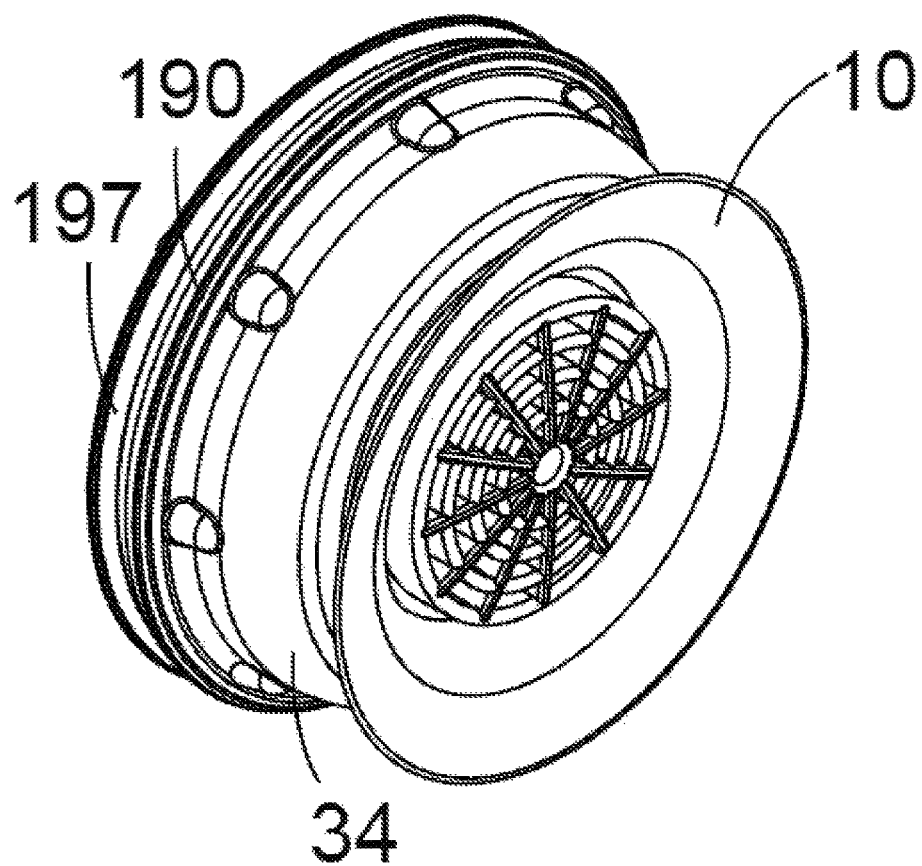
FIGS. 7A and 7B depict an isometric view of an alternate, contact charging sensor pod design with FIG. 7A depicting an attached gel pad and FIG. 7B depicting the charging sensor pod design and unattached gel pad or partially exploded view.
Figure 7B:
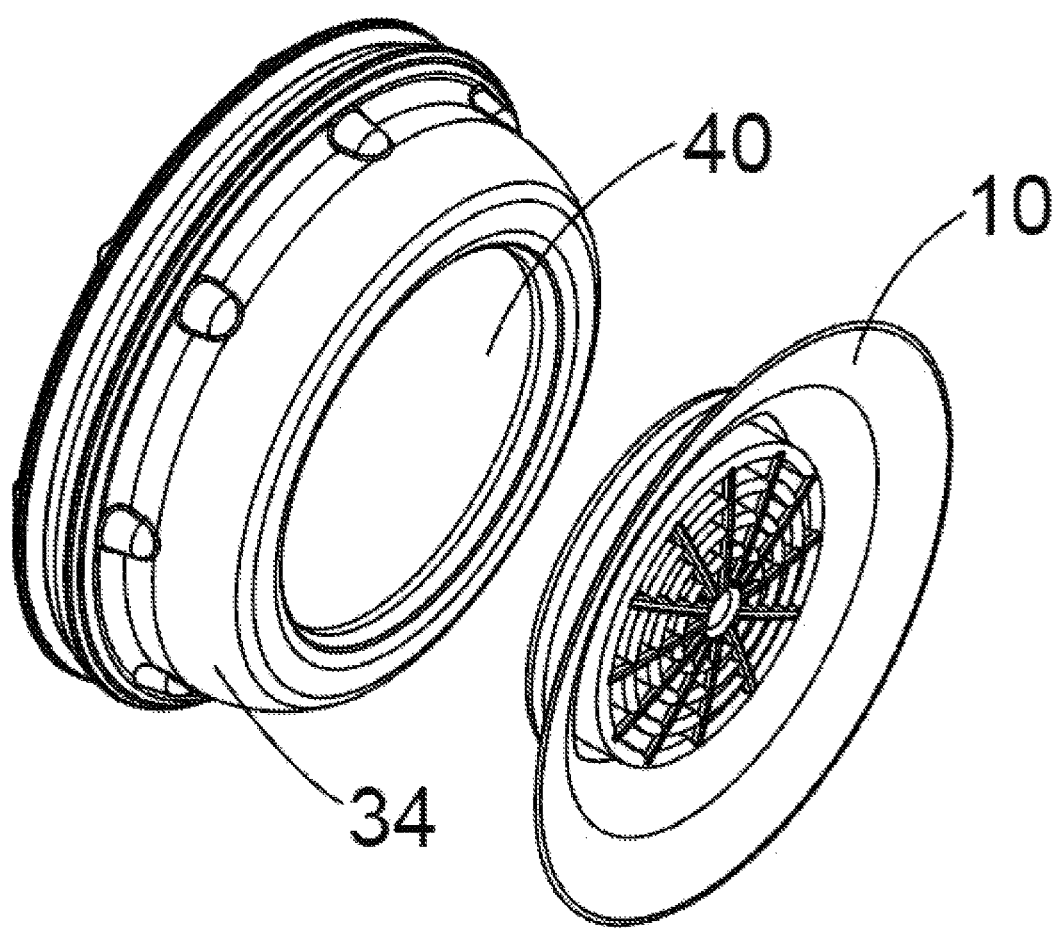

FIGS. 7A and 7B depict an alternative view of the contact charging sensor pod. The charging rings 190 and 197 are depicted in FIG. 7A, with the gel pad 10 in place. FIG. 7B depicts the charging pod with the gel pad 10 removed and depicting the piezoelectric sensor 40 where the gel pad 10 would otherwise contact.

Figure 8:
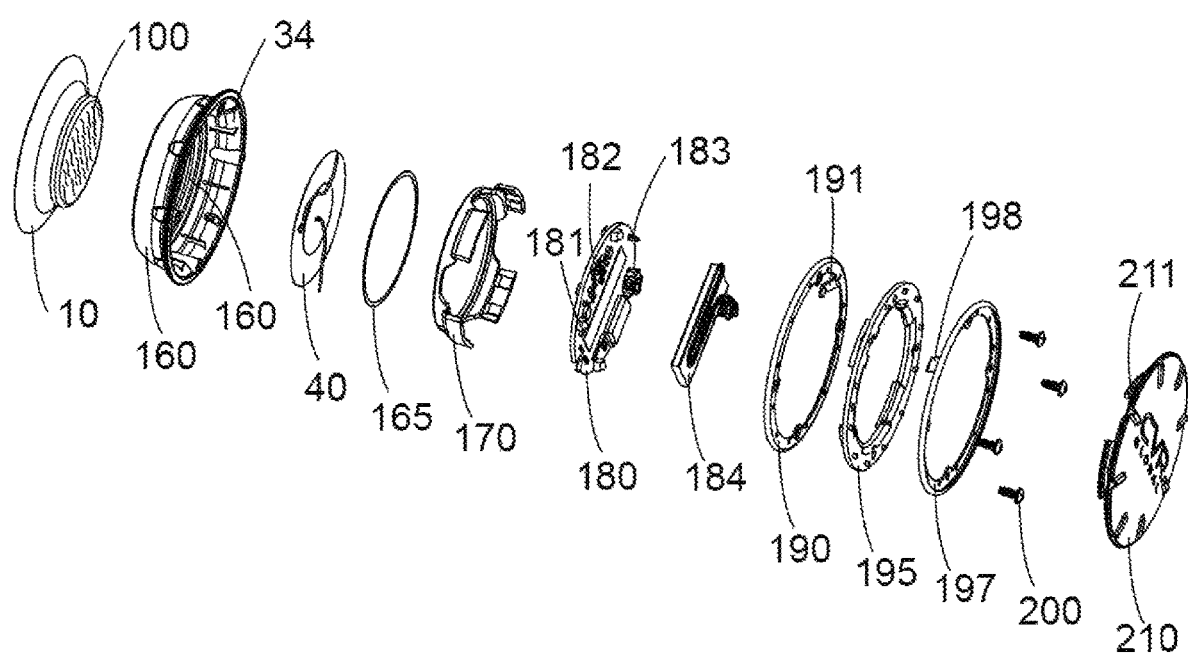
FIG. 8 depicts an exploded isometric view of an alternate, contact charging sensor pod design, its internal parts, and an unattached gel pad.

FIG. 8 depicts an exploded view of a charging sensor pod. The sensor pad 10 is depicted on the left most side, with an adhesive 100 provided therein. The pod cap 34 is depicted with a thermoplastic elastomer over molded material provided on outer and inner surfaces of the pod cap 34. The inclusion of the material herein aids in sound attenuation and soft touch features so as to eliminate background noise received by the piezoelectric unit 40. The piezoelectric unit 40 is provided with a flexible adhesive 165 which bonds the piezoelectric unit 40 to the PCB support 170. The PCB support 170 is connected to the PCB board 180. The PCB board 180 includes at least an LED 181, a spring pin negative 182 and a spring pin positive 183. The negative pin 182 connects to the metal connector tab 198 on the metal contact ring 197. The positive spring pin 183 connects to the connector tab 191 on contact ring 190. These components allow for simple and efficient contacts between the charging rings and the various electronic circuitry on the PCB board 180 to allow the device to function.

A rechargeable battery 184 is provided so as to power the device and can be connected to the PCB board 180 or simply affixed within the openings of the device therein. The insulator spacer 195 connects the rings 190 and 197 via heat stakes. The components can be affixed using threaded fasteners 200, or affixed with other means such as adhesives, welds, plastic, or other means as known to a person of ordinary skill in the art. The rear cap 210 includes several snap tabs 211 which connect the rear cap 210 to the insulator spacer 195, to ensure snug fit, but also access to internal components of the device.

In certain embodiments, the PCB board (also referred to as a base plate) is defined as having a top and a bottom. The top side of the PCB board then contacts to the PCB support 170. This PCB support 170 (base plate support) contacts directly to the piezo 40 with an adhesive 165. The PCB support 170 further comprises corresponding latches for contacting with the snap tabs 211 on the rear support (noise attenuating backing) 210.

As defined throughout, sound attenuating materials can be further secured within open spaces inside this assembly. Indeed, isolating sound from the piezo ensures that ambient noise and background noise is limited or eliminated and provides for a cleaner signal for processing.

Figure 9A:
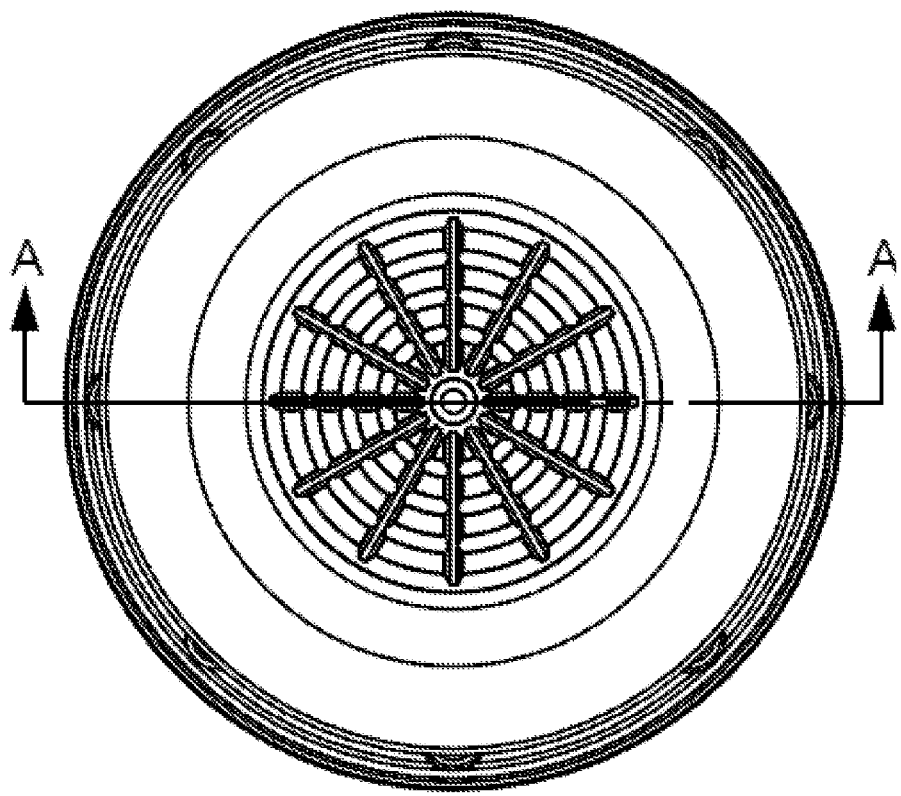
FIGS. 9A and 9B depict and alternative contact charging sensor pod design, with FIG. 9A depicting a front (patient facing side) view and FIG. 9B depicting a cross section through the gel pad based on the section line in FIG. 9A.
Figure 9B:
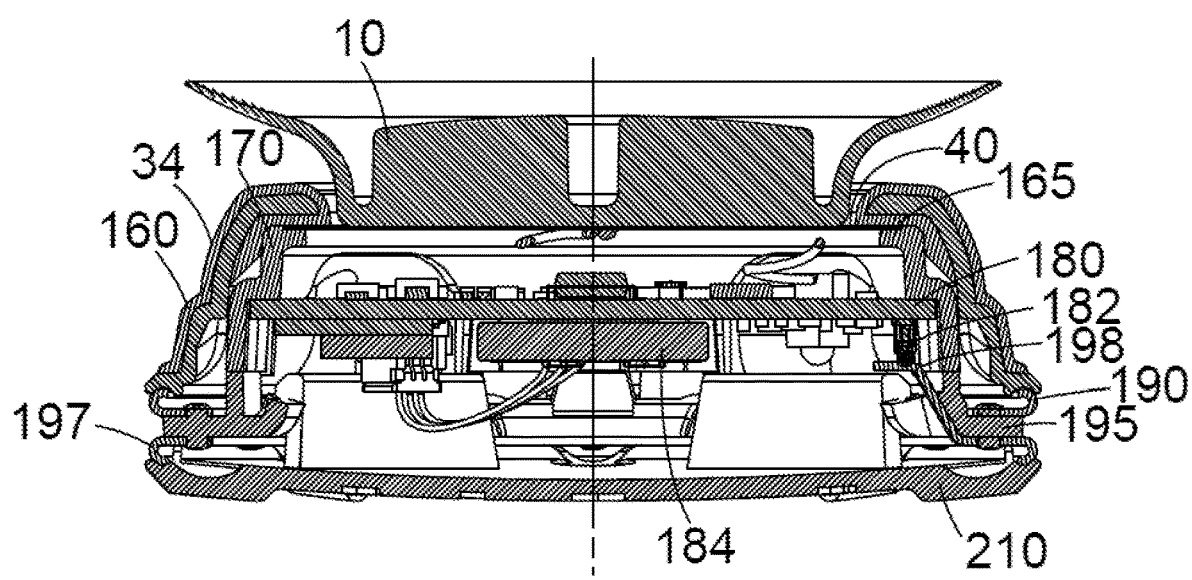

FIG. 9 provides a front or skin facing surface view of the charging sensor pod. A cross sectional line "A" is provided and depicted in FIG. 9B. FIG. 9B therefore depicts the gel pad 10, piezo 40, a flexible adhesive 165, a PCB Board 180, negative spring pin 182, connection tab 198, negative metal contact ring 190, and the insulator spacer 195 on the right hand side.

The rear cap 210 may be made of a sound absorbing material or include a coating or lining of sound attenuating material disposed of on the inner or outer face of the rear cap 210.

The battery 184 is provided centrally, while the left side depicts the positive metal contact 197, the thermoplastic outer molded material 160 as a portion of the pod cap 34. Further provided is the Piezoelectric and PCB support 170.

As is provided in prior figures, there is space or a void throughout the device that can be further filled with a sound attenuating material, such as a foam, gel, or other suitable material to limit background noise received by the piezo.

Figure 10A:
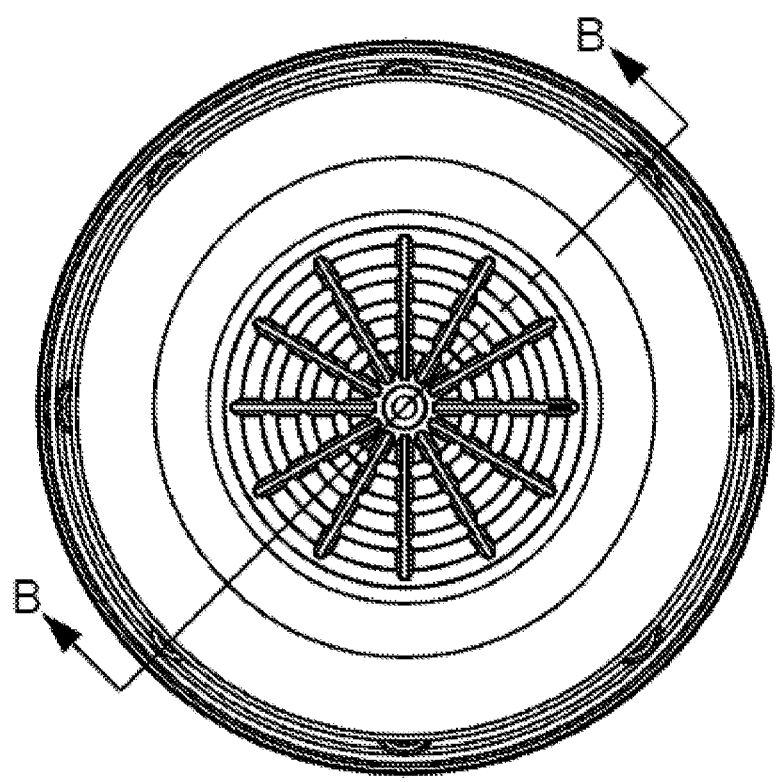
FIGS. 10A and 10B depict a further alternative assembly, with FIG. 10A depicting a front (patient facing side) view of an alternate, contact charging sensor pod design and attached gel pad with a section line, and FIG. 10B depicting a cross section through the attached gel pad based on the section line in FIG. 10A.
Figure 10B:
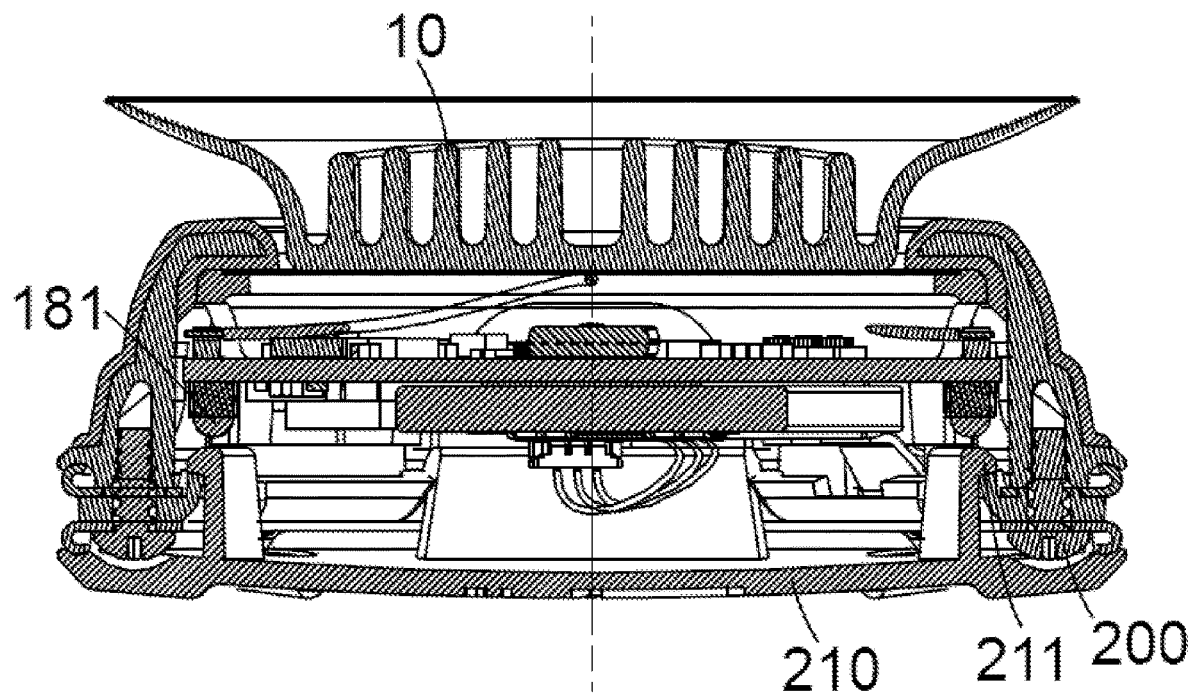

FIGS. 10A and 10B further depict an alternative gel pad 10 design, with the cross-sectional view through the B line. Depicted is an LED 181, and the snap tabs 211 corresponding to the rear cap 210.

Therefore, the device provides for a sensor pod that can be provided as a standalone testing device. The device can be directly placed onto a patient, and an optional pressure sensitive adhesive can be utilized to assist in holding the device onto the patient. Certain embodiments of the gel pad 10 also allow for generation of small suction forces to assist in holding the device to the skin of a patient. If, for example, a left artery is being tested, the patient can lay on the right side, having the left artery facing up, and then place the sensor pod onto the patient, where an adhesive and/or suction forces can assist in holding the sensor pod in position to perform a test.

In preferred embodiments, the device is used together with 1, 2 or 3 devices placed on the patient. In an orientation with a single device, the device is placed over an artery or vein on a patient that is being tested for blockage or stenosis. When using two devices together, there are two orientations. A first orientation places one device over the heart and a second over the area to be studied or tested for stenosis. A second orientation provides for a first device over one artery and a second device over a second artery. For example, the devices may be placed over the left and right carotid arteries, as a nonlimiting example of the positioning of the devices.

When using 3 devices, preferably a first device is placed over the heart and two additional devices placed over corresponding arteries on the body. For example, one over the heart and the second and third devices on the left and right carotid arteries. However, additional arterial may include the Vertebral artery, brachiocephalic artery, axillary artery, aorta, abdominal aorta, superior mesenteric artery, gonadal artery, inferior mesenteric artery, common iliac artery, external iliac artery, digital arteries, femoral artery, popliteal artery, anterior tibial artery, posterior tibial artery, dorsalis pedis, arcuate artery, subclavian artery, artic arch, coronary artery, thoracic aorta, gastric artery, splenic artery, hepatic artery, renal artery, radial artery, ulnar artery, deep palmar arch, superficial palmar arch, deep femoral artery.

Accordingly, the devices can be utilized in conjunction with methods to determine blockage or stenosis in the circulatory system of a human, by placing the devices on the skin adjacent to the target artery, wherein the device detects small sounds from the artery that can be detected by the highly sensitive piezo component, and wherein algorithms can then determine stenosis at the target artery.

What is claimed is:

1. A sensor pod assembly comprising:
a base plate having a top side and a bottom side, a piezoelectric unit, a battery, a noise attenuating backing, a wireless charging coil, a sound attenuating cap having an exterior shell and an interior sound attenuating material, a torus void, a ring shaped rear barrier, a sound attenuating barrier, and a sensor pad, said base plate comprising electronic circuitry connected to said battery, said piezoelectric unit and to said wireless charging coil, said piezoelectric unit attached to said top side of said base plate but provides a sound attenuating barrier below said piezo to provide a void space; and said wireless charging coil and said battery attached to said bottom side; said sound attenuating cap having a ring shape, having an inner and outer side wall and a circular opening providing access to the piezoelectric unit from the top side; positioned adjacent to said inner side wall is an interior sound attenuating material, having a different structure than the exterior shell of the sound attenuating cap, wherein a torus void is defined as a torus shaped structure adjacent to said piezoelectric unit; said noise attenuating backing engaged to the bottom side of the base plate; and wherein disposed below said base plate bottom side is the ring shaped rear barrier; and said sensor pad positioned within the circular opening of said sound attenuating cap and in contact with at least a portion of the piezoelectric unit.

2. The senor pod assembly of claim 1 further comprising a base plate support having a top and a bottom, said base plate support bottom engaged to the top side of the base plate and said piezoelectric unit attaching directly to said base plate support top.

3. The sensor pod assembly of claim 2 wherein said base plate support further comprises a securing ridge corresponding to a tab on said noise attenuating backing.

4. The sensor pod assembly of claim 2 wherein said sound attenuating cap comprises a securing component on an inner side having a paired securing component on said base plate support for selective attachment thereto.

5. The senor pod of claim 2 comprising an adhesive contact between said piezoelectric assembly and said base plate support.

6. The sensor pod assembly of claim 1 further comprising a sound attenuating material defined between the base plate bottom and said noise attenuating backing.

7. The sensor pod of claim 1 wherein said wireless charging coil comprising a positive charging contact and a negative charging contact sandwiched around an insulating spacer.

8. A sensor pod assembly comprising:
a base plate having a top and a bottom face, a base plate support having a top and bottom, an electronic circuitry, a piezoelectric device having a first side and a second side, a gel pad and a gel pad cap; wherein attached to the base plate is the electronic circuitry, comprising a battery, a wireless connection device, and a memory suitable to electronically run the sensor pod; said bottom of the base plate support attached to the top face of the base plate, and said second side of said piezoelectric device attached to the top of the base plate support, a gel pad having a piezoelectric device contacting surface and a skin facing surface; wherein a piezo void is defined below said piezoelectric device and above a sound attenuating barrier; and wherein disposed below the bottom of said base plate support is ring shaped rear barrier, and a base void define between the top of said base plate and the sound attenuating barrier, wherein said base void is filled with a sound attenuating material; wherein the piezoelectric device contacting surface is in contact with the first side of the piezoelectric device; and a gel pad cap comprising an outer layer and an inner layer, with said inner layer attached to the base plate with corresponding threaded components on the base plate and the inner layer of said gel pad cap.

9. The sensor pod assembly of claim 8 wherein said gel pad comprises a circumferential flange on the piezo contacting surface, said circumferential flange in intimate contact with said gel pad cap, thereby securing said gel pad into position.

* * * * *